(12) United States Patent
Gonzales et al.

(10) Patent No.: US 11,229,468 B2
(45) Date of Patent: Jan. 25, 2022

(54) MIXING SYRINGE AND METHOD OF USE

(71) Applicant: Vivex Biologics Group, Inc., Atlanta, GA (US)

(72) Inventors: Silvia Daniela Gonzales, Miami Lakes, FL (US); Shabnam Namin, Miami, FL (US); William Blake Martin, Smyrna, GA (US); Timothy Ganey, Tampa, FL (US)

(73) Assignee: Vivex Biologics Group, Inc., Atlanta, GA (US)

( * ) Notice: Subject to any disclaimer, the term of this patent is extended or adjusted under 35 U.S.C. 154(b) by 310 days.

(21) Appl. No.: 16/437,389

(22) Filed: Jun. 11, 2019

(65) Prior Publication Data

US 2020/0390485 A1 Dec. 17, 2020

(51) Int. Cl.

| | |
|---|---|
| *A61B 17/88* | (2006.01) |
| *A61M 3/00* | (2006.01) |
| *A61M 5/46* | (2006.01) |
| *A61F 2/46* | (2006.01) |
| *A61F 2/28* | (2006.01) |

(52) U.S. Cl.
CPC ........ *A61B 17/8833* (2013.01); *A61F 2/4601* (2013.01); *A61F 2/4644* (2013.01); *A61M 3/005* (2013.01); *A61M 5/46* (2013.01); *A61B 2017/8838* (2013.01); *A61F 2002/2835* (2013.01)

(58) Field of Classification Search
CPC .. A61B 2017/8838; A61M 3/005; A61M 5/46
See application file for complete search history.

(56) References Cited

U.S. PATENT DOCUMENTS

| | | | |
|---|---|---|---|
| 3,140,078 A | 7/1964 | Krahe et al. | |
| 3,348,546 A | 10/1967 | Roberts et al. | |
| 4,277,184 A * | 7/1981 | Solomon | A61B 17/8822 366/139 |
| 4,469,153 A | 9/1984 | Morrisette | |
| 4,966,468 A | 10/1990 | Werner | |
| 5,009,645 A * | 4/1991 | Silver | A61M 5/3158 604/207 |
| 5,842,785 A | 12/1998 | Brown et al. | |
| 6,120,174 A * | 9/2000 | Hoag | B01F 11/0082 366/139 |
| 6,592,247 B1 | 7/2003 | Brown et al. | |
| 6,974,247 B2 | 12/2005 | Frei et al. | |

(Continued)

*Primary Examiner* — Nicholas W Woodall
(74) *Attorney, Agent, or Firm* — David L. King (57) ABSTRACT

A syringe mixing device has a cylindrical syringe housing, an end cap, a nozzle cap, a removable stir rod mixer assembly, a large mouth funnel, and optional locking clip. The cylindrical syringe housing has an internal chamber for holding material, a distal end and a proximal end. Adjacent the proximal end is a pair of finger grips. The end cap has a proximal end for attaching to the distal end of the syringe housing. The end cap has a nozzle configured to pass material ejected from the syringe housing. The nozzle cap is for sealing the nozzle. The large mouth funnel is configured to fasten at a throat end to the distal end of the cylindrical syringe housing. The funnel has a slope shaped chamber configured to receive and pass material for mixing into the internal chamber of the syringe housing. The syringe mixing device further has a removable plunger.

18 Claims, 8 Drawing Sheets

(56) References Cited

U.S. PATENT DOCUMENTS

| | | | |
|---|---|---|---|
| 7,168,847 B2 | 1/2007 | Frei et al. | |
| 7,879,002 B2 | 2/2011 | Jessop | |
| 9,180,417 B2 | 11/2015 | Greter | |
| 9,220,577 B2 | 12/2015 | Jessop et al. | |
| 2006/0116644 A1* | 6/2006 | Norton | A61M 5/31511 604/187 |
| 2012/0330229 A1* | 12/2012 | Greter | B01F 11/0082 604/82 |
| 2014/0098629 A1* | 4/2014 | Greter | A61B 17/8827 366/184 |
| 2016/0128752 A1* | 5/2016 | Greter | B01F 15/0237 606/94 |
| 2018/0147355 A1* | 5/2018 | Larsen | A61M 5/2066 |

\* cited by examiner

MIXING SYRINGE AND METHOD OF USE

FIELD OF THE INVENTION

The present invention relates to mixing devices generally, more particularly to a syringe that incorporates a mixing feature and once material is mixed can be converted to a filled syringe with a standard plunger for dispensing the mixed material.

BACKGROUND OF THE INVENTION

The use of mixing devices to uniformly dispense different materials has been done using a variety of techniques and mechanical devices. Hand mixing materials and expecting a homogenous mixture uniformly dispersed varies widely and is virtually unsuited for applications requiring a uniform blending.

Currently, grafts made of bone particles or fibers, bone gels and cells, generally stem cells, are mixed in the operating room by trained technicians wearing sterile gloves and blending the materials with their palms. This is a tedious and time-consuming procedure fraught with technical problems. First, the graft consistency varies widely due to different mixing methods and levels of experience and competence of the technician. Secondly, portions of the graft material are wasted when left on the gloved palms. In the case of stem cell laden grafts, any waste is very undesirable and costly. A third problem is maintaining sterility during mixing.

The present invention overcomes these deficiencies allowing a mixing device to uniformly blend and mix these graft materials uniformly with virtually no loss and in an aseptic manner to avoid contamination or damage to the homogenous blend and to allow a conversion of the mixing device into a delivery device for direct implantation.

SUMMARY OF THE INVENTION

A syringe mixing device has a cylindrical syringe housing, an end cap, a nozzle cap, a removable stir rod mixer assembly and a large mouth funnel. The cylindrical syringe housing has an internal chamber for holding material, a distal end and a proximal end. Adjacent the proximal end is a pair of finger grips. The end cap has a proximal end for attaching to the distal end of the syringe housing. The end cap has a nozzle configured to pass material ejected from the syringe housing. The nozzle cap is for sealing the nozzle. The large mouth funnel is configured to fasten at a throat end to the distal end of the cylindrical syringe housing. The funnel has a slope shaped chamber configured to receive and pass material for mixing into the internal chamber of the syringe housing. The slope shaped chamber of the funnel is preferably conical. The syringe mixing device further has a removable plunger.

The removable stir rod mixer assembly has a stir shaft with a mixing paddle at a distal end of the stir shaft, a seal, a seal support and a handle. The mixing paddle can have four equally sized mixing blades. The mixing blades are equally spaced relative to a longitudinal axis of the stir shaft. Each mixing blade has an arcuate shaped end. Each arcuate shaped end is circumferentially centered on each mixing blade. The seal has a central hole for receiving the stir shaft. The seal is sized to slide in and seal the internal chamber of the syringe housing. The seal support configured with a central hole for receiving the stir shaft. The seal support is configured to abut a proximal end of the seal to provide rigidity. The handle is configured to attach to a proximal end of said stir shaft and provide a means to assist in rotating the stir shaft to move the plurality of mixing paddles.

The syringe mixing device further includes one or more locking clips. Each locking clip is configured to lock onto the proximal end of the syringe housing. The locking clip has a central hollow cylinder for passing the stir shaft for movement linearly and rotationally. A length (L) of the central hollow cylinder limits the travel of the stir rod mixing shaft and the mixing paddles linear movement inside the internal chamber. The length (L) of the locking clip limits the volume of material to fill the internal chamber.

The removable plunger has an elastomeric seal at the distal end of the plunger. In one embodiment, the distal end of the cylindrical syringe housing has an opening diameter equal to a diameter of the internal chamber. The distal end of the cylindrical syringe housing can be threaded, and the end cap is threaded to fasten to the threads of the distal end of the syringe housing. Similarly, the throat end of the large mouth funnel has threads to fasten to the distal end of the syringe housing.

BRIEF DESCRIPTION OF THE DRAWINGS

The invention will be described by way of example and with reference to the accompanying drawings in which:

FIGS. 3A, 3B and 3C are a first set of plan views.

FIGS. 4A, 4B and 4C are a second set of plan views similar to the first set, but with a short locking clip attached.

DETAILED DESCRIPTION OF THE INVENTION

Figure 1A:
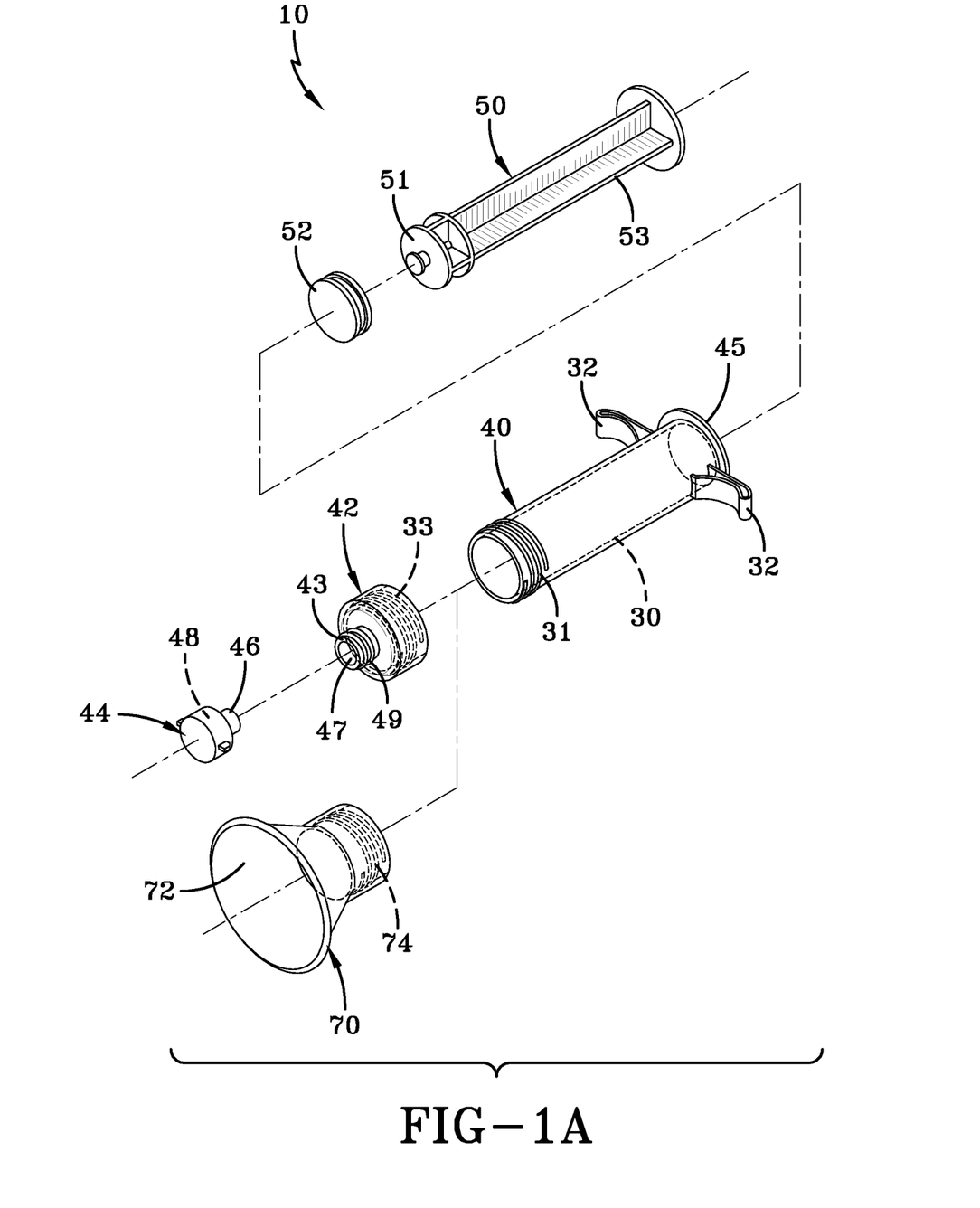
FIG. 1A is an exploded perspective view of the syringe mixing device of the present invention with the removable plunger.
Figure 1B:
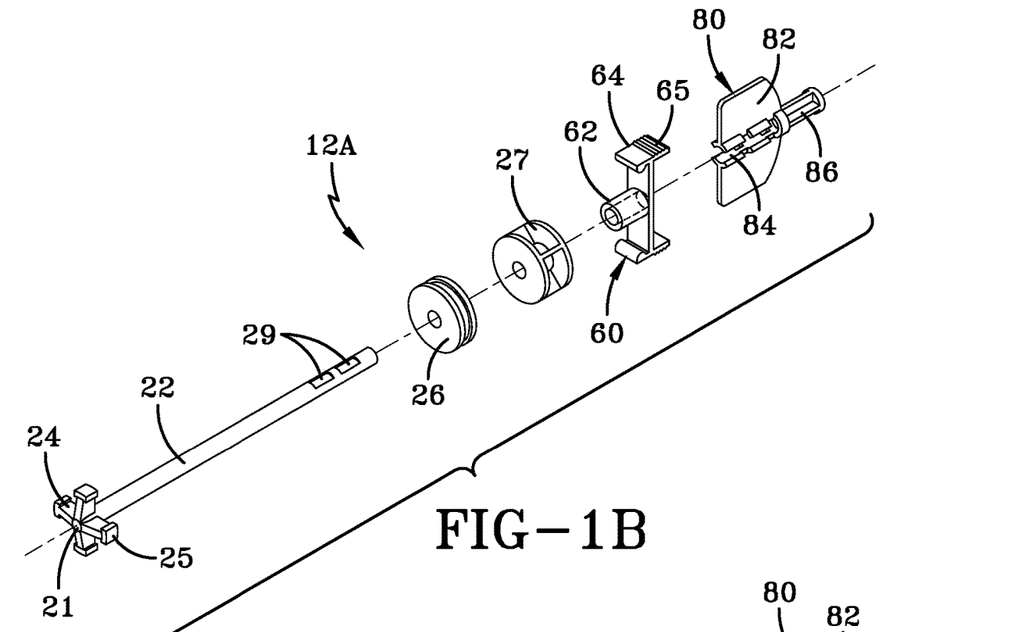
FIG. 1B is an exploded perspective view of the removable stir rod assembly with the short locking clip.
Figure 1C:
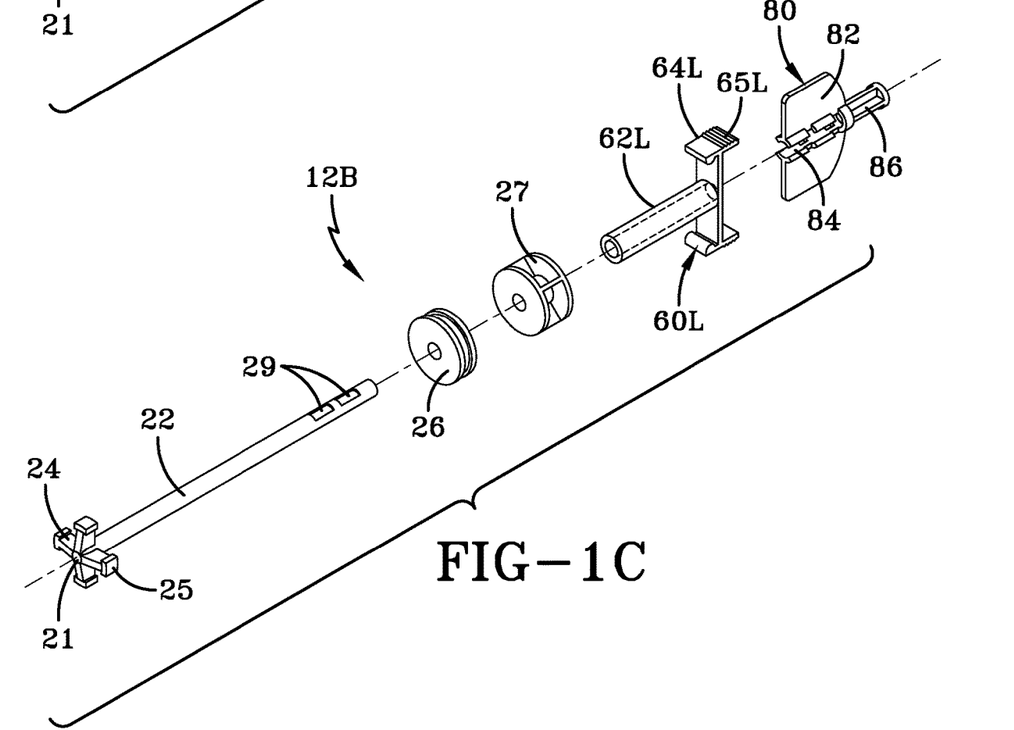
FIG. 1C is an exploded perspective view of the removable stir rod assembly with the long locking clip.
Figure 2:
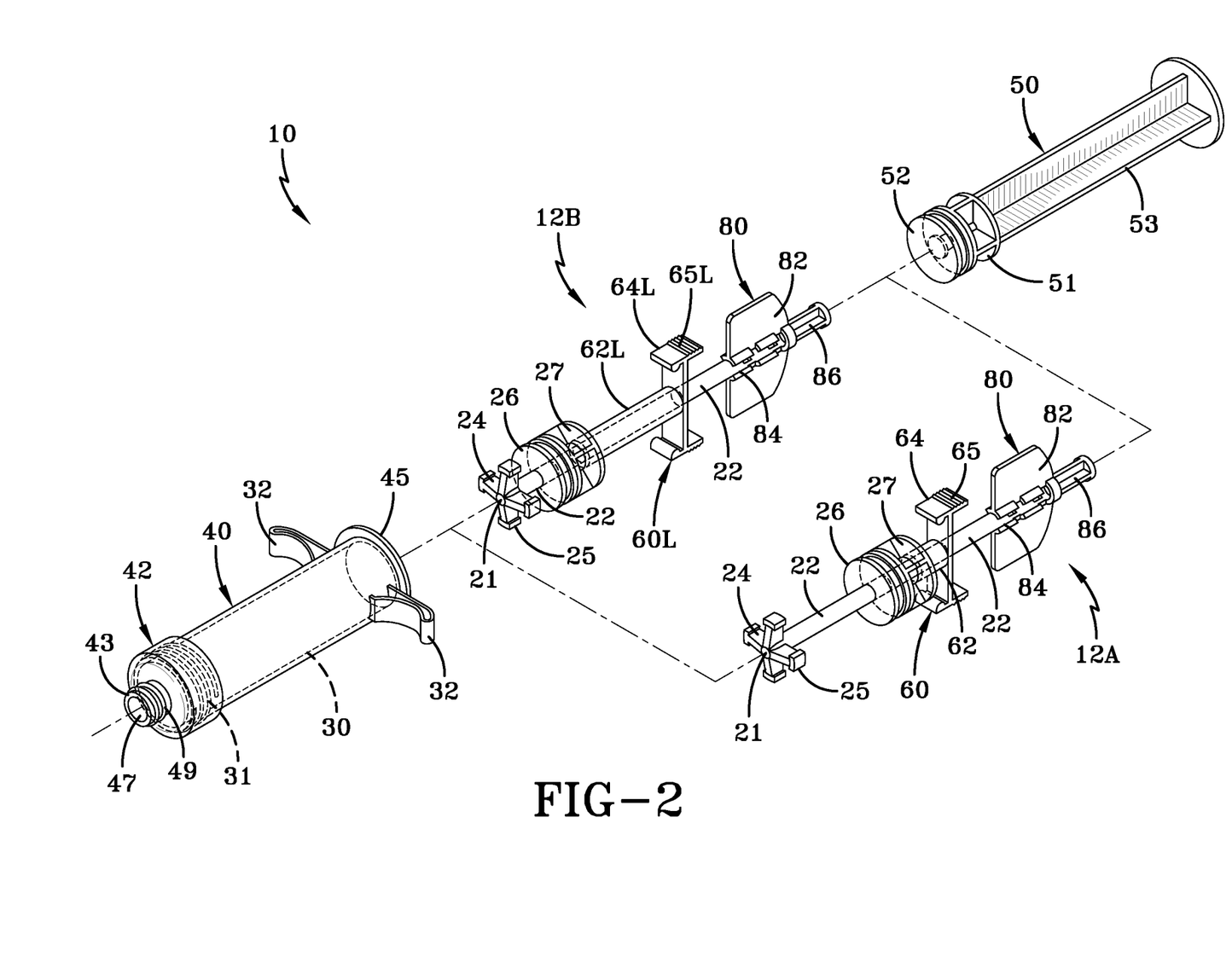
FIG. 2 is a view taken from FIGS. 1A-1C wherein the removable stir rod assembly is shown separated from the syringe housing in two views, one with a large locking clip attached to the assembly and a second with a short locking clip attached to the assembly. The removable syringe plunger is separately shown illustrating how the device is convertible from a mixer device to a syringe.

With reference to FIGS. 1A-2, the syringe mixer device 10 of the present invention is illustrated. In FIG. 1A, an exploded view of the components of the syringe mixer device 10 with the removable plunger 50, funnel 70, nozzle cap 44, end cap 42 and syringe housing 40. FIG. 1B is an exploded view showing the components of the stir rod mixer assembly 12A. Stir rod mixer assembly 12A includes the mixing paddle 21, stir shaft 22, seal 26, seal support 27, short locking clip 60 and handle 80. FIG. 1C is an exploded view showing the components of the stir rod mixer assembly 12B which is identical to stir rod mixer assembly 12A other than long locking clip 60L is used in place of short locking clip 60.

In FIG. 2, the removable stir rod assembly 12A, 12B is illustrated as a complete assembly showing the long locking clip option 12B and short locking clip option 12A that are used with the syringe housing as well as the removable plunger 50. As shown in FIG. 2, the stir rod mixer assembly 12A, 12B has a locking clip 60, 60L attached to the stir shaft 22. The locking clip 60, 60L has a hollow cylindrical tube 62, 62L of a specific length (L). The length (L) of the hollow cylindrical tube 62, 62L limits the linear distance the stir rod mixer assembly 12A, 12B can travel inside the syringe housing 40. On the lower portion of FIG. 2 is shown the syringe housing 40 with the end cap 42 threaded onto the distal end of the syringe housing 40. The end cap 42 having a threaded nozzle 43 for ejecting material. On the opposite side of FIG. 2 in the upper corner, is a removable plunger 50 having a plunger shaft 53 and a rubber seal or stopper 52 backed by a stopper support 51 as illustrated. This removable plunger 50 is not used initially with the present invention and is shown as a separate component which will be added later.

With reference to the syringe housing 40, at a proximal end is shown an enlarged lip or ring 45 around the external surface, this ring 45 is used to facilitate locking the locking clip 60, 60L onto the syringe housing 40. As illustrated in FIG. 1, each locking clip 60, 60L has lateral ends 64 at a proximal end adjacent the hollow cylindrical tube 62, 62L such that the lateral ends 64 can be pushed up against the proximal end of the syringe housing 40 and snapped onto the ring 45 of the syringe housing 40 at the lateral ends of the locking clip 60, 60L. As shown the locking clip lateral ends 64 have serrations 65 that allow for flexible movement of the ends 64 so they will flex upwardly when pressed by the user, this allows for easy attachment and detachment of the locking clip 60, 60L and the syringe housing 40.

The internal chamber 30 of the syringe housing 40 is shown at a constant diameter and is circular in cross section. At the distal end, the syringe housing 40 is shown with external threads 31 that facilitate attachment of the end cap 42 which has complimentary female threads 33 that will engage the syringe housing 40 and be removably attached or detached as needed. Furthermore, the end cap 42 has an ejection nozzle 43 that allows for material to be pushed through the nozzle 43. The nozzle 43 has an internal surface 47 that is open to the syringe housing 40 when attached. This internal opening or lumen 47 is plugged by a nozzle cap 44 as illustrated in FIG. 1. The nozzle cap 44 has an internal shaft 46 that will plug the lumen 47 and fit inside the lumen 47 with an outer portion having internal threads 48 that will engage the threads 49 of the nozzle 43 and will be tightly and securely attached thereto sealing the nozzle 43.

Referring to the removable stir rod mixer assembly 12A, 12B, as shown in FIGS. 1B and 1C in its various components. The removable stir rod mixer assembly 12A, 12B includes a longitudinally extending stir shaft 22 with mixing paddle 21 at the distal end. The mixing paddle 21 has mixing blades 24 that are shown in an "X" or cross configuration with end feet 25 that are arcuately curved to complimentarily match the internal chamber 30 of the cylindrical syringe housing 40. The mixing paddle 21 is rigidly fixed to the stir shaft 22. Adjacent the stir shaft 22 is a rubber stopper or seal 26 and a seal support 27 which are slid up to the mixing paddle 21 along the stir shaft 22, this is shown more clearly in FIG. 2. The proximal end of the stir shaft 22 has a pair of openings or slots 29 that will engage tabs 84 on a handle 80. The handle 80, as shown, fits over the stir shaft 22 and is snapped into place on the slots 29 locking the handle 80 into position. The handle 80 facilitates rotation of the stir rod mixer assembly 12A, 12B. The flat portion 82 of the handle 80 provides a means of pulling the stir rod mixer assembly 12A, 12B fore and aft inside the syringe housing 40 to mix the materials inside the internal chamber 30. The handle end 86 has a cylindrical shape which allows the user to grasp and spin the entire stir rod mixer assembly 12A, 12B to disperse material as will be illustrated below.

Figure 3A:
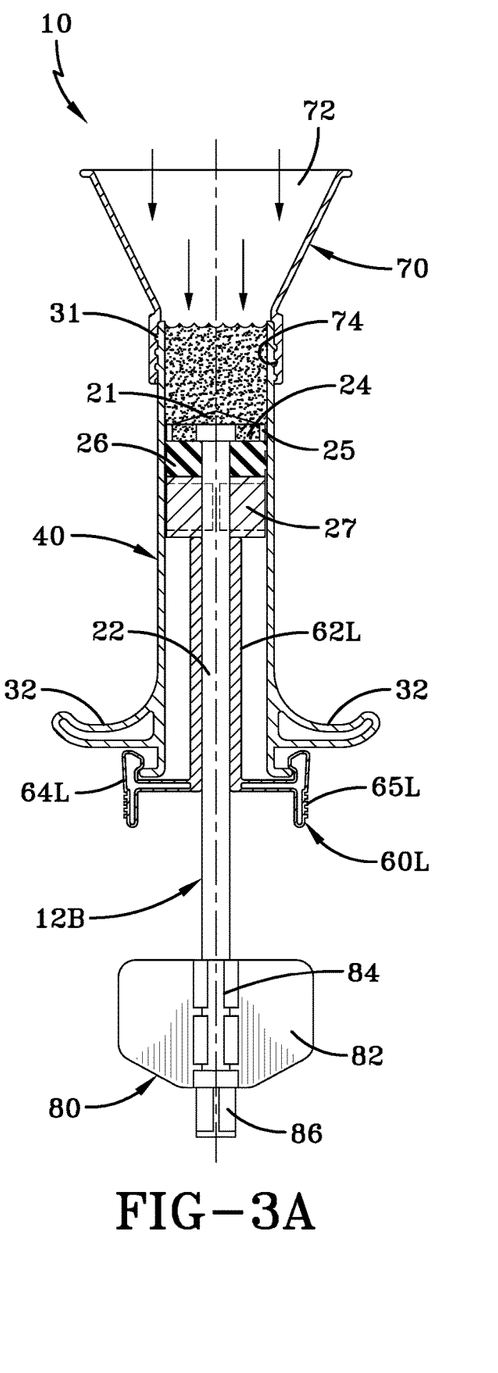
FIG. 3A shows the large mouth funnel attached to the distal end of the syringe housing with the stir rod mixer assembly inserted in the proximal end of the syringe housing affixed to a long locking clip, the arrows at the funnel depicting how the material to be mixed is added.
Figure 3B:
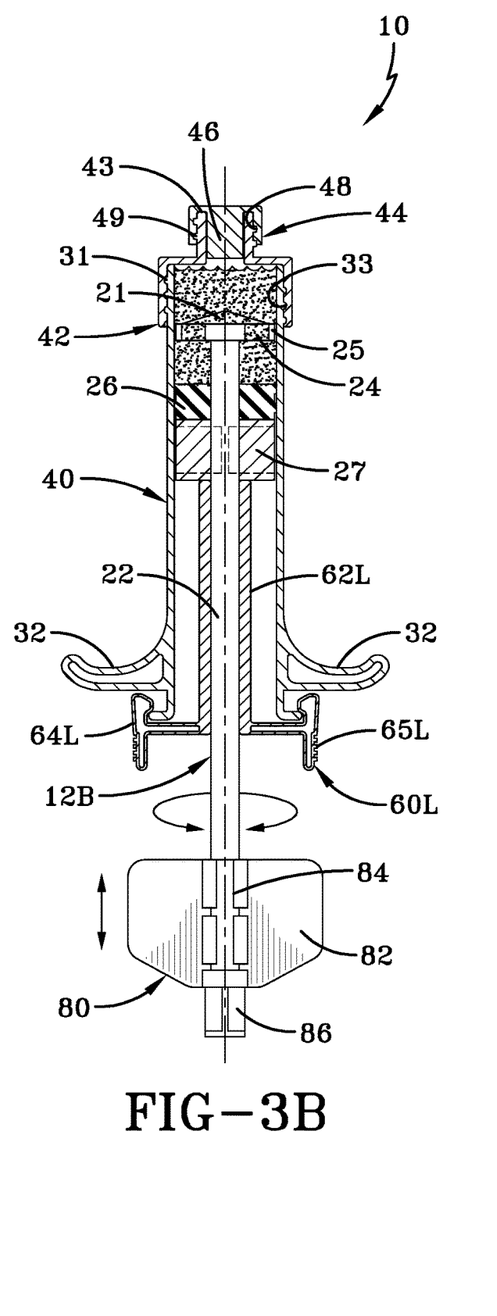
FIG. 3B shows the end cap with nozzle cap replacing the large mouth funnel and the arrows showing the rotational and linear mixing movements of the stir rod mixer assembly.
Figure 3C:
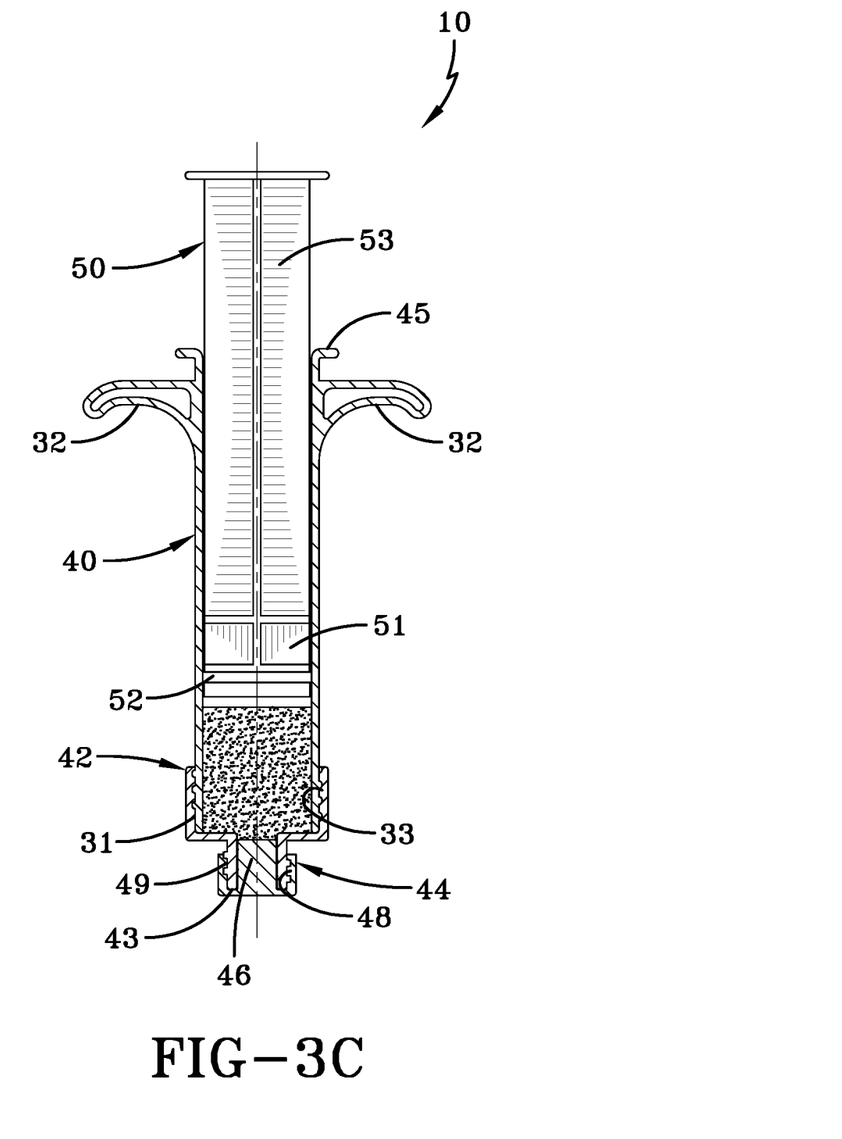
FIG. 3C shows the replacement stir rod mixer assembly with the syringe plunger into the syringe housing with a capped nozzle. Once the material has been blended and homogenously mixed, the syringe is readied for discharging the material for implantation.

With reference to FIG. 3A, with the end cap 42 removed, a large mouth funnel 70 is shown threaded onto the external threads 31 at the distal end of the syringe housing 40. The large mouth funnel 70 has a slope shape with an enlarged opening 72 at one end to allow materials to be funneled directly into the syringe housing 40 and threads 74 to attach to the syringe housing 40, as illustrated in FIG. 3A. The materials 2, 3, once placed into the syringe housing 40 internal chamber 30, can thereafter be thoroughly mixed by rotating and linearly moving the stir rod mixer assembly 12B, as shown in FIG. 3B. After the funnel 70 has performed its function of allowing material to be easily transmitted into the internal chamber 30 it can be, and preferably is removed with the end cap 42 placed back onto the syringe housing 40 with the nozzle cap 44 attached to the nozzle 43 so it is sealed tightly. At this point the user, having all the constituent components of the material to be mixed inside the internal chamber 30, can rotate the stir rod mixer assembly 12B rapidly spinning the mixing paddle 21 to thoroughly mix the material 2, 3. In addition to rotating, the mixing paddle 21 can be moved linearly up and down within the cylindrical syringe housing 40 to allow the materials 2, 3 to more evenly disperse the material throughout the internal chamber 30. As shown in FIGS. 3A and 3B, the stir rod mixer assembly 12B is limited in its travel by length (L) of the hollow cylindrical tube 62L of the locking clip 60L. As shown, the locking clip 60L has been snapped onto the syringe housing 40 directly above the finger grips 32 that are positioned on the external surface of the syringe housing 40 to facilitate injecting material when a plunger 50 is applied later, as shown in FIG. 3C. As shown in FIG. 3C, once the material 2, 3 has been thoroughly mixed, the end cap is shown in its proper position, the plunger 50 can be placed back into the syringe housing 40. In doing so, it may be necessary to hold the syringe housing 40 slightly upward once the plunger 50 is started to prevent any entrapped air and allow the air to evacuate through the slightly loosened nozzle cap 44 until the plunger 50 contacts the material. At this point, the thoroughly mixed and blended material, which could be bone particles, bone gel, in combination with a fluid such as a sterile fluid, stem cells or other materials for implantation which has been thoroughly homogenized and blended into a homogenous material by using the stir rod mixer assembly 12A, 12B and is ready for implantation.

Figure 4A:
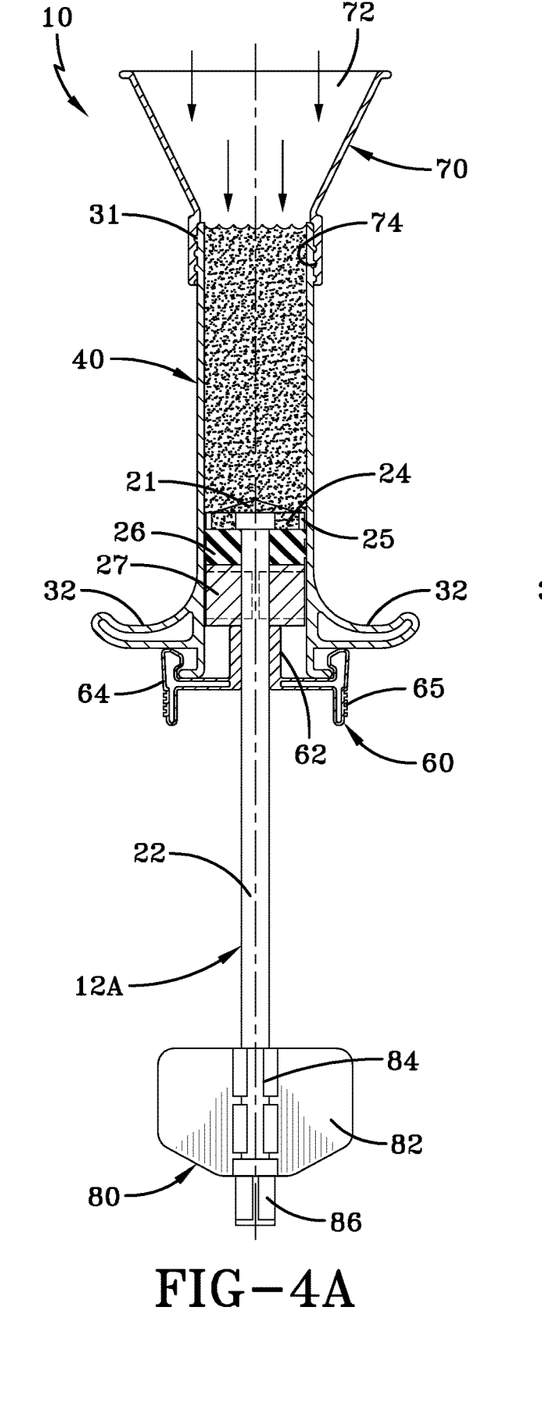
FIG. 4A shows the large mouth funnel attached to the distal end of the syringe housing with the stir rod mixer assembly inserted in the proximal end of the syringe housing affixed to a long locking clip, the arrows at the funnel depicting how the material to be mixed is added.
Figure 4B:
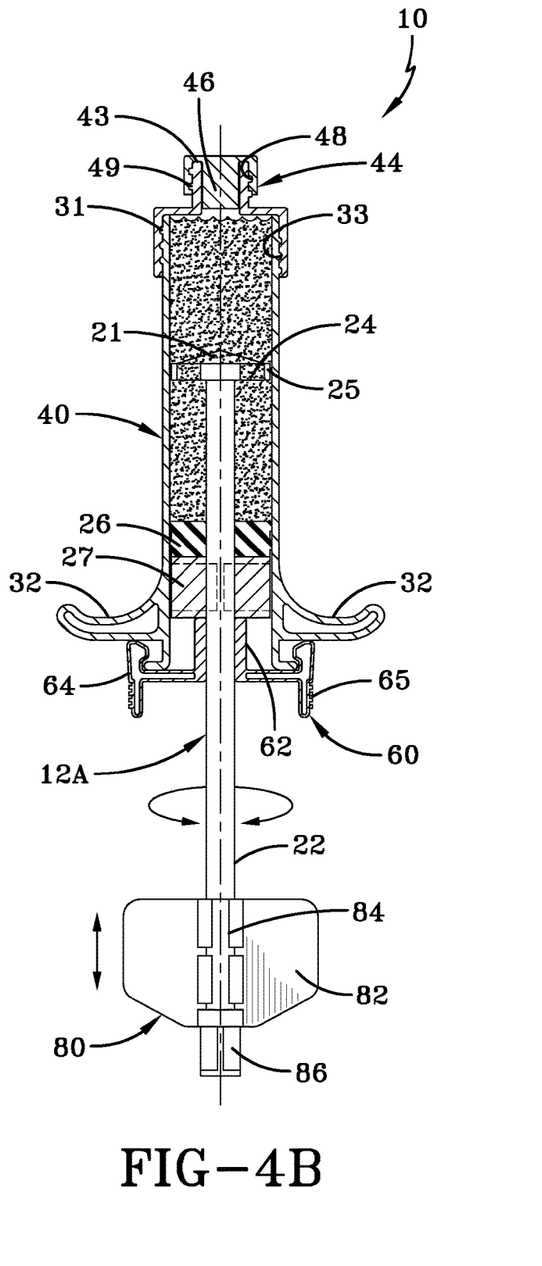
FIG. 4B shows the end cap with nozzle cap replacing the large mouth funnel and the arrows showing the rotational and linear mixing movements of the stir rod mixer assembly.
Figure 4C:
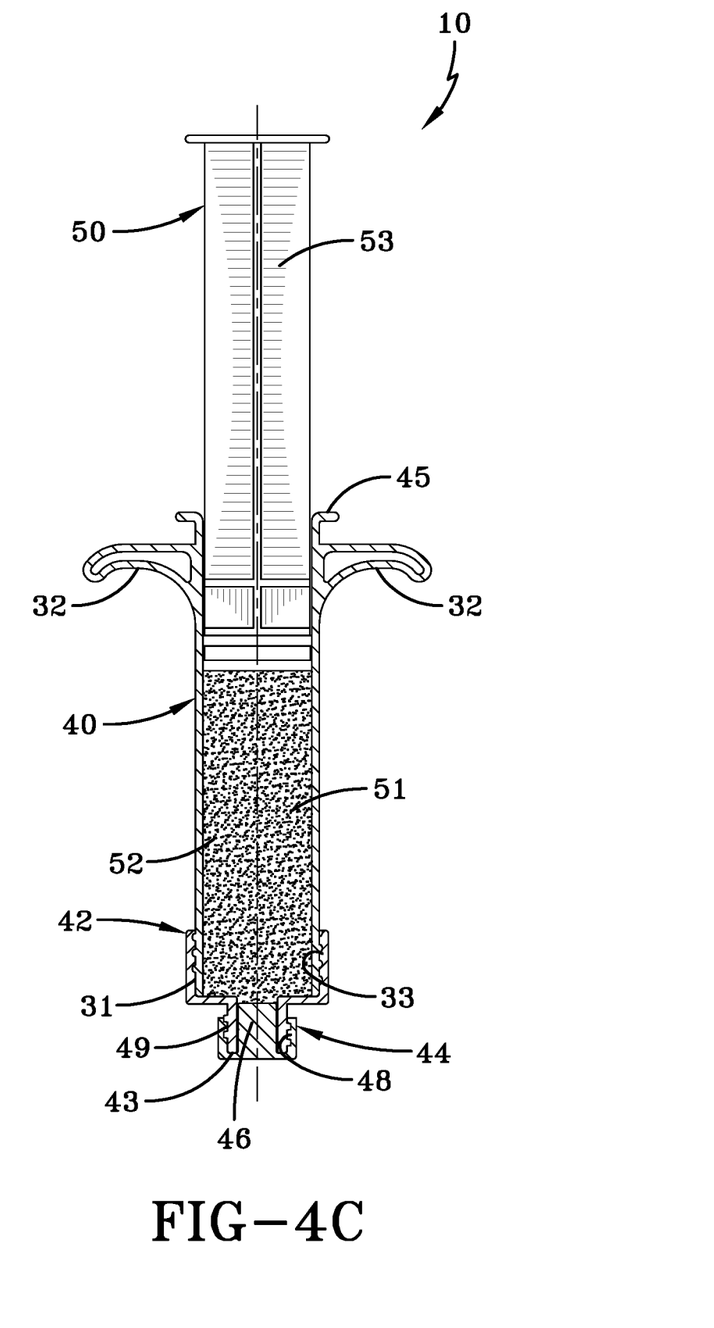
FIG. 4C shows the replacement stir rod mixer assembly with the syringe plunger into the syringe housing with a capped nozzle. Once the material has been blended and homogenously mixed, the syringe is readied for discharging the material for implantation.

With reference to FIGS. 4A, 4B and 4C, the same procedure as shown in FIGS. 3A-3C is illustrated using stir rod mixer assembly 12A with the shorter locking clip 60. In FIGS. 4A and 4B, the locking clip 60 with a shorter hollow cylindrical tube 62 is used. In this case, a larger volume of material can be added to the internal chamber 30 using the funnel 70 as previously mentioned. The stirring method is repeated with a larger amount of travel available with stir rod mixer assembly 12A allowing the paddle 21 to move further up and down in the internal chamber 30 to thoroughly mix the constituents of the material being blended and mixed. As shown in FIG. 4B, the end cap 42 replaces the funnel 70 for stirring and mixing. All of this is done in a self-contained system that is sterile and the procedure can be done very aseptically. Once this is accomplished, the plunger 50 can be placed in the syringe housing 40, as previously noted.

Figure 5A:
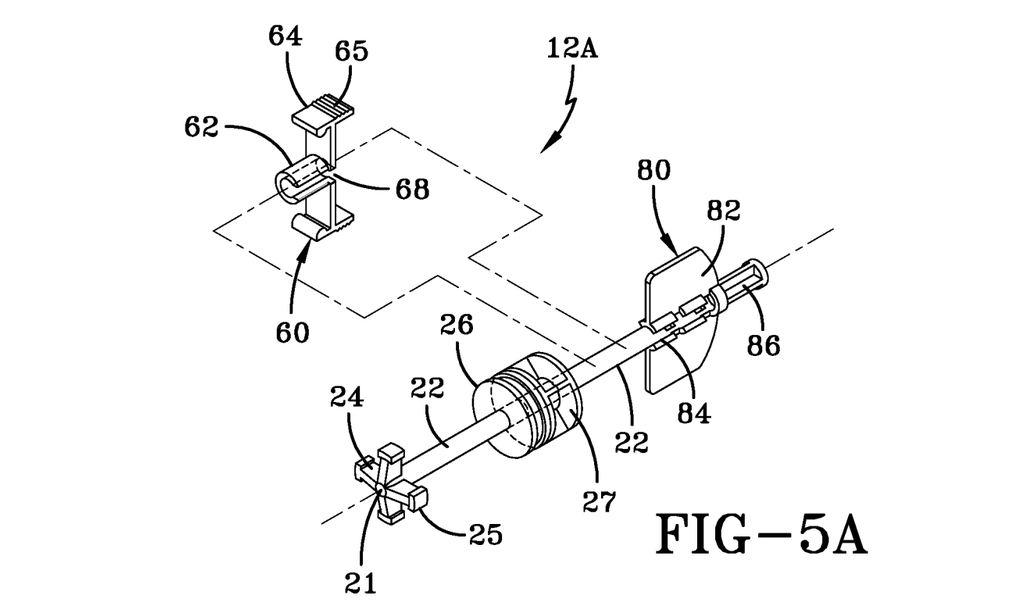
FIGS. 5A and 5B show an alternative locking clip in the short and the long versions wherein the hollow cylindrical tube has a longitudinal slot with allows the locking clips to snap onto the rod shaft as offset to being slid over the rod shaft end.
Figure 5B:
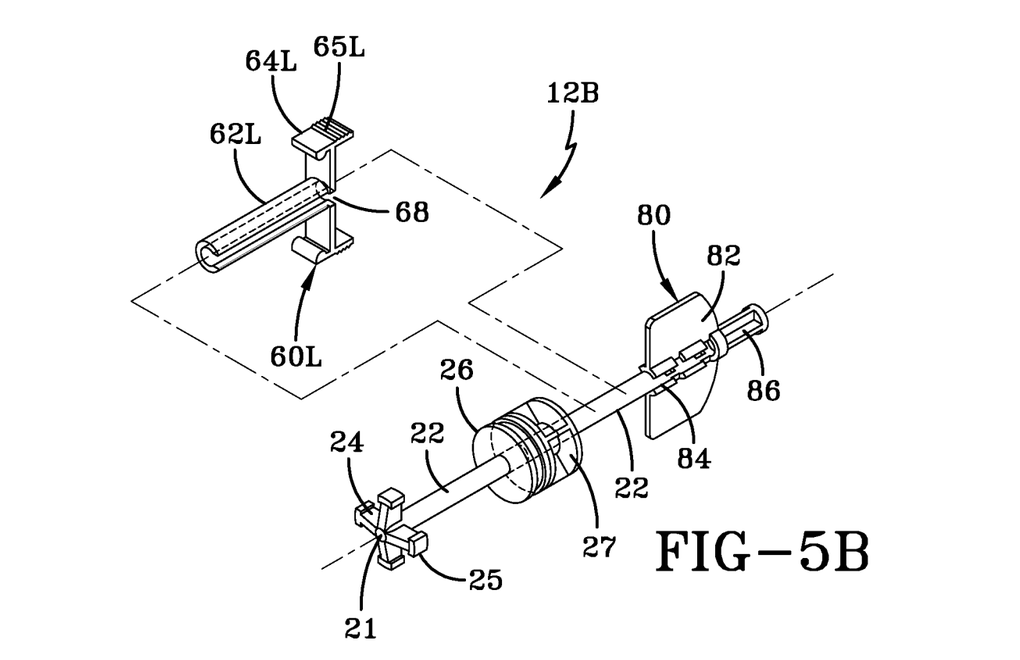

In FIGS. 5A and 5B, an alternative embodiment is shown where the locking clip 60, 60L has a slot 68 along the longitudinal portion of the hollow cylindrical tube 62, 62L. This slot 68 allows for the locking clip to be snapped onto the stir shaft 22. This can facilitate the selection of the various locking clips 60, 60L. As shown, two lengths are provided, however, multiple lengths can be provided. Each corresponding to a different volume or cc's that can be contained within the syringe housing 40 and be properly mixed. As shown, the slot 68 is simply snapped onto the side of the stir shaft 22 and is flexible enough to allow the hollow 62 to flex open slightly so that the locking clip 60, 60L can engage the stir shaft 22 and snap into position. Preferably the stir shaft 22 is round or circular so that it does not impede rotation of the stir rod mixer assembly 12A, 12B when using a locking clip 60, 60L with a slot 68 feature. These and other alternatives can be used with the present invention.

As shown, the nozzle cap 44 and end cap 42 are detached from the syringe housing 40 while the stir rod mixer assembly 12A, 12B is positioned at the proximal end of the syringe housing 40. The locking clip 60, 60L is then clipped to the proximal end to keep the stir rod mixer assembly 12A, 12B at the desired position. The graft material is poured into the internal chamber 30. The funnel 70 could be screwed on using threads 74 to the distal end to aid pouring the graft material. Once the material is added, the funnel 70 is removed and the end cap 42 and nozzle cap 44 are screwed onto the distal end of the syringe housing 40. The user manually rotates the stir rod mixer assembly 12A, 12B while going up and down the barrel. The position of the seal 26 in the syringe housing 40 limits the room available for mixing graft material. The locking clip 60, 60L also prevents the seal 26 and stir rod mixer assembly 12A, 12B from detaching from the syringe housing 40 during mixing of graft materials. Once the materials are mixed, the locking clip 60, 60L, the stir rod mixer assembly 12A, 12B and the seal 26 are removed. The plunger 50 is inserted into the proximal end of the syringe housing 40. The material can be extruded by removing the end cap 42 or the nozzle cap 44. Any remaining material in the nozzle 43 and end cap 42 can be extruded by using the pin or handle end 86 located at the end of the stir rod mixer assembly 12A, 12B.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A syringe mixing device comprising:
    a cylindrical syringe housing having an internal chamber for holding material, a distal end and a proximal end, the proximal end has an enlarged lip or ring around an external surface of the cylindrical syringe housing and adjacent the proximal end being a pair of finger grips;
    an end cap with a proximal end for attaching to the distal end of the cylindrical syringe housing, the end cap having a nozzle configured to pass material ejected from the cylindrical syringe housing;
    a nozzle cap for sealing the nozzle;
    a removable stir rod mixer assembly for mixing material in the internal chamber of the cylindrical syringe housing, wherein the removable stir rod mixer assembly comprises:
        a stir shaft with a mixing paddle at a distal end of the stir shaft, the mixing paddle having a plurality of mixing blades;
        a seal with a central hole for receiving the stir shaft, the seal sized to slide in and seal the internal chamber of the cylindrical syringe housing;
        a seal support configured with a central hole for receiving the stir shaft, the seal support configured to abut a proximal end of the seal to provide rigidity; and
        a handle configured to attach to a proximal end of said stir shaft and provide a means to assist in rotating the stir shaft to move the plurality of mixing paddles;
    a large mouth funnel configured to fasten at a throat end to the distal end of the cylindrical syringe housing, the funnel having a slope shaped chamber configured to receive and pass material for mixing into the internal chamber of the cylindrical syringe housing; and
    wherein the syringe mixing device includes one or more locking clips, each locking clip configured to lock onto the enlarged lip or ring at the proximal end of the cylindrical syringe housing; the locking clip having a central hollow cylinder for passing the stir shaft for movement linearly and rotationally, a length (L) of the central hollow cylinder limits the travel of the mixing paddles linear movement inside the internal chamber, each locking clip has lateral ends at a proximal end adjacent a hollow cylindrical tube such that the lateral ends can be pushed up against the proximal end of the cylindrical syringe housing and snapped onto the enlarge lip or ring of the cylindrical syringe housing at the lateral ends of the locking clip.

2. The syringe mixing device of claim 1 further comprises a removable plunger.

3. The syringe mixing device of claim 2 wherein the removable plunger has an elastomeric seal at the distal end of the plunger.

4. The syringe mixing device of claim 1 wherein the lateral ends of the locking clip have serrations that allow for flexible movement of the lateral ends which flex when pressed allowing for easy attachment and detachment of the locking clip to the lip or ring of the cylindrical syringe housing.

5. The syringe mixing device of claim 4 wherein a length (L) of the hollow cylindrical tube of the locking clip limits the volume of material to fill the internal chamber.

6. The syringe mixing device of claim 4 wherein the volume of material to fill the internal chamber is increased by using a shorter length of the hollow cylindrical tube and conversely reduced by using a longer length of the hollow cylindrical tube.

7. The syringe mixing device of claim 4 wherein the locking clip has a slot along a longitudinal portion of the hollow cylindrical tube, the slot allows for the locking clip to be snapped onto the stir shaft of the removable stir and mixer assembly.

8. The syringe mixing device of claim 7 wherein the cylindrical hollow tube with the slot is configured to be snapped onto the stir shaft and is flexible enough to allow the hollow cylindrical tube to flex open slightly so that the locking clip can engage the stir shaft and snap into position.

9. The syringe mixing device of claim 8 wherein the stir shaft is round or circular so that it does not impede rotation of the stir rod mixer assembly when using a locking clip with a slot feature.

10. The syringe mixing device of claim 1 wherein the distal end of the cylindrical syringe housing has an opening diameter equal to a diameter of the internal chamber.

11. The syringe mixing device of claim 1 wherein the distal end of the cylindrical syringe housing is threaded.

12. The syringe mixing device of claim 11 wherein the end cap is threaded to fasten to the threads of the distal end of the cylindrical syringe housing.

13. The syringe mixing device of claim 11 wherein the throat end of the large mouth funnel has threads to fasten to the distal end of the cylindrical syringe housing.

14. The syringe mixing device of claim 3 wherein the mixing paddle has four equally sized mixing blades.

15. The syringe mixing device of claim 3 wherein the mixing blades are equally spaced relative to a longitudinal axis of the stir shaft.

16. The syringe mixing device of claim 3 wherein each mixing blade has an arcuate shaped end.

17. The syringe mixing device of claim 3 wherein each arcuate shaped end is circumferentially centered on each mixing blade.

18. The syringe mixing device of claim 1 wherein the large mouth funnel is conical.

* * * * *